(12) United States Patent
Assmann et al.

(10) Patent No.: US 6,180,655 B1
(45) Date of Patent: Jan. 30, 2001

(54) SULFONYL BENZAZOLONES

(75) Inventors: Lutz Assmann, St. Peter Ording; Hans-Ludwig Elbe, Wuppertal; Robert Markert, Köln; Ralf Tiemann, Leverkusen; Klaus Stenzel, Düsseldorf, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/284,338

(22) PCT Filed: Oct. 6, 1997

(86) PCT No.: PCT/EP97/05473

§ 371 Date: Apr. 9, 1999

§ 102(e) Date: Apr. 9, 1999

(87) PCT Pub. No.: WO98/17665

PCT Pub. Date: Apr. 30, 1998

(30) Foreign Application Priority Data

Oct. 17, 1996 (DE) .............................. 196 42 865

(51) Int. Cl.[7] .......................... A01N 43/80; A01N 43/76; C07D 413/12
(52) U.S. Cl. ............................................ 514/375; 548/221
(58) Field of Search .............................. 514/375; 548/221

(56) References Cited

U.S. PATENT DOCUMENTS

| | | | |
|---|---|---|---|
| 2,922,794 | 1/1960 | Model et al. | 260/304 |
| 3,839,349 | 10/1974 | Wagner et al. | 260/304 |

FOREIGN PATENT DOCUMENTS 2074561   11/1981   (GB) .

OTHER PUBLICATIONS

Cram and Hammond, "Organic Chemistry", McGraw Hill Book Co., NY (1964) 2nd Ed. pp 565–567.*
Chem. Ber. 93, (month unavailable) 1960, pp. 1331–1339.
J. Med. Chem. Sep. 9, 1966, p. 719.
Heterocycles, 24, (month unavailable) 1986, p. 1625.
J. Heterocycles Chem., 28, Jun.–Jul. 1991, p. 1933.
Synthesis, (month unavailable) 1984, p. 254.
J. Heterocycles Chem., Aug. 1981, pp. 997–1006.
Patent Abstracts of Japan, vol. 5, No. 94, Jun. 19, 1981 & JP 56 036474 A (Hokko Chemical Co. Ltd), Apr. 9, 1981.

* cited by examiner

*Primary Examiner*—Patricia L. Morris
(74) *Attorney, Agent, or Firm*—Joseph C. Gil

(57) ABSTRACT

Sulphonylbenzazolones of the formula

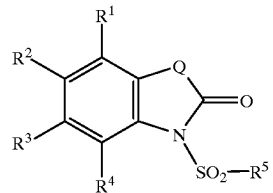

(I)

in which

R[1], R[2], R[3], R[4], R[5] and Q are each as defined in the description.

a process for preparing these compounds and their use as microbicides in crop protection and in the protection of materials.

5 Claims, No Drawings

SULFONYL BENZAZOLONES

The present invention relates to novel sulphonylbenzazolones, to a process for their preparation and to their use as microbicides in crop protection and in the protection of materials.

TECHNICAL FIELD OF THE INVENTION

It is already known that certain sulphonylbenzazolones have fungicidal properties (cf. DE-A 2 101 150). Thus, for example, N,N-dimethyl-7-nitro-2-oxo-5-trifluoro-methyl-benzothiazole-3-sulphonamide can be used for controlling fungi. The activity of this compound is good, but at times leaves something to be desired at low application rates.

BACKGROUND OF THE INVENTION

Detailed Description of the Invention

This invention, accordingly, provides novel sulphonyl-benzazolones of the formula

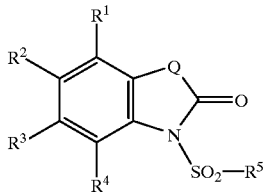

(I)

in which $R^1$, $R^2$, $R^3$ and $R^4$ independently of one another each represent hydrogen, halogen, cyano, nitro, alkyl, halogenoalkyl, alkoxy, halogenoalkoxy, alkylthio, halogenoalkylthio, alkylsulphinyl, halogenoalkylsulphinyl, alkylsulphonyl, halogenoalkylsulphonyl, optionally substituted cycloalkyl, hydroxycarbonyl, alkylcarbonyl, alkoxycarbonyl, cycloalkylcarbonyl, cycloalkoxycarbonyl, represent —Z—K$^6$ or

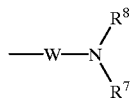

in which $R^6$ represents optionally substituted aryl or represents optionally substituted heterocyclyl, z represents a direct bond, represents —CH$_2$—, O, S, SO$_2$ or CO or
represents —CO—O— where the oxygen atom is linked to R$^6$, or
represents —SO$_2$—O— where the sulphur atom is linked to R$^6$, or
represents —S—CH$_2$—SO$_2$— where the sulphur atom of the thio group is linked to R$^6$, or
represents —NH—SO$_2$— where the sulphonyl group is linked to R$^6$, $R^7$ and $R^8$ independently of one another represent hydrogen, alkyl, halogenoalkyl, alkoxyalkyl, alkylcarbonyl, optionally substituted aryl, optionally substituted arylcarbonyl, optionally substituted aryl-sulphonyl, optionally substituted arylaminocarbonyl or optionally substituted arylmethylsulphonyl or $R^7$ and $R^8$ together with the nitrogen atom to which they are attached represent an optionally alkyl-substituted heterocyclic ring which may contain an additional oxygen atom or an alkylimino group and W represents a direct bond, a sulphonyl group or a carbonyl group, or $R^1$ and $R^2$, or $R^2$ and $R^3$, or $R^3$ and $R^4$ together each represent an optionally substituted alkylene chain having 3 or 4 members, in which one or two (non-adjacent) carbon atoms may be replaced by oxygen atoms, $R^5$ represents optionally substituted unsaturated heterocyclyl and Q represents oxygen or sulphur.

Furthermore, it was found that sulphonylbenzazolones of the formula (I) are obtained when benzazolones of the formula

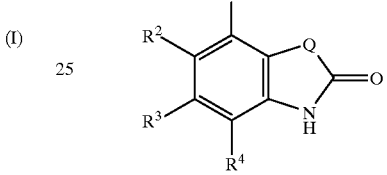

(II)

in which $R^1$, $R^2$, $R^3$, $R^4$ and Q are each as defined above are reacted with a sulphonyl halide of the formula

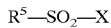 $R^5$—SO$_2$—X (III)

in which $R^5$ is as defined above and

X represents halogen,
if appropriate in the presence of an acid binder and if appropriate in the presence of a diluent.

Finally, it was found that the sulphonylbenzazolones of the formula (I) have very good microbicidal properties and can be employed in crop protection and also in the protection of materials.

Surprisingly, the compounds according to the invention exhibit better fungicidal activity than N,N-dimethyl-7-nitro-2-oxo-5-trifluoromethyl-benzothiazole-3-sulphonamide, an active compound of the prior art having a similar structure and the same direction of action.

Formula (I) provides a general definition of the compounds according to the invention.

$R^1$, $R^2$, $R^3$ and $R^4$ independently of one another each preferably represent hydrogen, fluorine, chlorine, bromine, iodine, cyano, nitro, straight-chain or branched alkyl having 1 to 8 carbon atoms, straight-chain or branched halogenoalkyl having 1 to 6 carbon atoms and 1 to 5 identical or different halogen atoms, straight-chain or branched alkoxy having 1 to 8 carbon atoms, straight-chain or branched halogenoalkoxy having 1 to 6 carbon atoms and 1 to 5 identical or different halogen atoms, straight-chain or branched alkylthio having 1 to 8 carbon atoms, straight-chain or branched halogenoalkylthio having 1 to 6 carbon atoms and 1 to 5 identical or different halogen atoms, straight-chain or branched alkylsulphinyl having 1 to 8 carbon atoms, straight-chain or branched halogenoalkylsulphinyl having 1 to 6 carbon atoms and 1 to 5 identical or different halogen atoms, straight-chain or branched alkylsulphonyl having 1 to 8 carbon atoms, straight-chain or branched halogenoalkylsulphonyl having 1 to 6 carbon atoms and 1 to 5 identical or different halogen atoms, cycloalkyl having 3 to 6 carbon atoms which is optionally mono- to pentasubstituted by identical or different halogens and/or alkyls having 1 to 4 carbon atoms, represents hydroxy-carbonyl, alkylcarbonyl having 1 to 6 carbon atoms in the straight-chain or branched alkyl moiety, alkoxycarbonyl having 1 to 6 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety, represents —Z—$R^6$ or

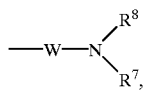

$R^6$ preferably represents aryl having 6 to 10 carbon atoms, each of these radicals being mono- to trisubstituted by identical or different substituents from the group consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and/or halogenoalkylsulphonyl having 1 to 4 carbon atoms and 1 to 5 identical or different halogen atoms.

$R^6$ additionally preferably represents an unsaturated heterocyclyl radical having 5 or 6 ring members and 1 to 3 heteroatoms such as nitrogen, oxygen and/or sulphur, it being possible for these radicals to be mono- to trisubstituted by identical or different substituents from the group consisting of halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 3 carbon atoms in the alkoxy moiety, cycloalkyl having 3 to 6 carbon atoms, cyano and/or nitro.

Z also preferably represents a direct bond, and also represents —$CH_2$—, O, S, $SO_2$ or CO or
represents —CO—O— where the oxygen atom is linked to $R^6$, or
represents —$SO_2$—O— where the sulphur atom is linked to $R^6$, or
represents —S—$CH_2$—$SO_2$— where the sulphur atom of the thio group is linked to $R^6$, or
represents —NH—$SO_2$— where the sulphonyl group is linked to $R^6$.

$R^7$ and $R^8$ independently of one another each preferably represent hydrogen, straight-chain or branched alkyl having 1 to 6 carbon atoms, straight-chain or branched halogenoalkyl having 1 to 6 carbon atoms and 1 to 5 identical or different halogen atoms, straight-chain or branched alkoxyalkyl having 1 to 4 carbon atoms in the alkoxy moiety and 1 to 4 carbon atoms in the alkyl moiety, alkylcarbonyl having 1 to 6 carbon atoms in the straight-chain or branched alkyl moiety, aryl having 6 to 10 carbon atoms, arylcarbonyl having 6 to 10 carbon atoms in the aryl moiety, arylsulphonyl having 6 to 10 carbon atoms, arylaminocarbonyl having 6 to 10 carbon atoms in the aryl moiety or represents arylmethylsulphonyl having 6 to 10 carbon atoms in the aryl moiety, it being possible for each of the abovementioned aryl radicals to be mono- to trisubstituted by identical or different substituents from the group consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and/or halogenoalkylsulphonyl having 1 to 4 carbon atoms and 1 to 5 identical or different halogen atoms.

$R^7$ and $R^8$ together with the nitrogen atom to which they are attached additionally also preferably represent a heterocyclic ring having 5 or 6 ring members which may contain an additional oxygen atom or a $C_1$–$C_4$-alkylimino group and which is optionally mono- to trisubstituted by alkyl having 1 to 4 carbon atoms.

W also preferably represents a direct bond, a sulphonyl group or a carbonyl group.

$R^1$ and $R^2$, or $R^2$ and $R^3$, or $R^3$ and $R^4$ together each also preferably represent an alkylene chain having 3 or 4 members in which one or two (non-adjacent) carbon atoms may be replaced by oxygen atoms and which is optionally mono- to hexasubstituted by halogen, alkyl having 1 to 4 carbon atoms and/or halogenoalkyl having 1 to 4 carbon atoms and 1 to 5 halogen atoms.

$R^5$ preferably represents an unsaturated heterocyclyl radical having 5 or 6 ring members and 1 to 3 heteroatoms such as oxygen, nitrogen and/or sulphur, it being possible for these radicals to be optionally mono- to trisubstituted by identical or different substituents from the group consisting of halogen, cyano, nitro, amino, hydroxyl, formyl, carboxyl, carbamoyl, thiocarbamoyl, alkyl having 1 to 4 carbon atoms, alkoxy having 1 to 4 carbon atoms, alkylthio having 1 to 4 carbon atoms, alkylsulphonyl having 1 to 4 carbon atoms, halogenoalkyl having 1 to 4 carbon atoms and 1 to 5 halogen atoms, halogenoalkoxy having 1 to 4 carbon atoms and 1 to 5 halogen atoms, halogenoalkylthio having 1 to 4 carbon atoms and 1 to 5 halogen atoms, halogenoalkylsulphonyl having 1 to 4 carbon atoms and 1 to 5 halogen atoms, alkylamino having 1 to 4 carbon atoms, dialkylamino having 1 to 4 carbon atoms in each of the two alkyl chains, alkylcarbonyl having 1 to 4 carbon atoms in the alkyl moiety, alkylcarbonyloxy having 1 to 4 carbon atoms in the alkyl moiety, alkoxycarbonyl having 1 to 4 carbon atoms in the alkoxy moiety, alkylsulphonyloxy having 1 to 4 carbon atoms, hydroximinoalkyl having 1 to 4 carbon atoms, alkoximinoalkyl having 1 to 4 carbon atoms in each of the two alkyl chains, halogenoalkoxycarbonyl having 1 to 4 carbon atoms and 1 to 5 halogen atoms in the halogenoalkoxy moiety and/or cycloalkyl having 3 to 6 carbon atoms.

Q preferably represents oxygen or sulphur.

$R^1$, $R^2$, $R^3$ and $R^4$ independently of one another each particularly preferably represent hydrogen, fluorine, chlorine, bromine, cyano, nitro, represent methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, acetyl, acetyloxy, methoxycarbonyl, ethoxycarbonyl, cyclopropyl, cyclobutyl, cyclopentyl, cyclohexyl, represent —Z—$R^6$ or

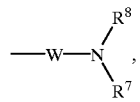

$R^6$ particularly preferably represents phenyl which may be mono- to trisubstituted by identical or different substituents from the group consisting of fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, difluoromethylsulphinyl and/or trifluoromethylsulphonyl.

$R^6$ also particularly preferably represents pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5 triazinyl, pyridinyl, pyrimidinyl, pyrazinyl or pyridazinyl, it being possible for each of these radicals to be mono- or disubstituted by identical or different substituents from the group consisting of fluorine, chlorine, methyl, methoxy, trifluoromethyl, difluoromethoxy and trifluoromethoxy.

Z also particularly preferably represents a direct bond, and also—$CH_2$—, O, S, $SO_2$, CO or
represents—CO—O— where the oxygen atom is linked to $R^6$, or
represents—$SO_2$—O— where the sulphur atom is linked to $R^6$, or
represents—S—$CH_2$—$SO_2$— where the sulphur atom of the thio group is linked to $R^6$, or
represents—NH—$SO_2$— where the sulphonyl group is linked to $R^6$.

$R^7$ and $R^8$ independently of one another each particularly preferably represent hydrogen, methyl, ethyl, n-propyl, isopropyl or phenyl.

$R^7$ and $R^8$ together with the nitrogen atom to which they are attached additionally also particularly preferably represent pyrrolidinyl, piperidinyl, morpholinyl or 4-methyl-piperazinyl.

W also particularly preferably represents a direct bond, a sulphonyl group or a carbonyl group.

$R^1$ and $R^2$, or $R^2$ and $R^3$, or $R^3$ and $R^4$ together each also particularly preferably represent the groupings —$CF_2$—O—$CF_2$—, —O—$CF_2$—O—, —O—$CF_2$—CHF—O—, —O—CHF—CHF—O—, —O—$CF_2$—$CF_2$—O—, —O—$CF_2$—CFCl—O—or —O—CFCl—CFCl—O—.

$R^5$ particularly preferably represents pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridinyl, pyrimidinyl, pyrazinyl or pyridazinyl, it being possible for these radicals to be mono-, di- or optionally even trisubstituted by identical or different substituents from the group consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, cyclopropyl, methoxy, ethoxy, n- or i-propoxy, methylthio, ethylthio, n- or i-propylthio, methylsulphonyl, ethylsulphonyl, trifluoromethyl, difluoromethoxy, trifluoromethoxy, difluoromethylthio, trifluoromethylthio or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and/or ethoxyiminoethyl.

Q also particularly preferably represents oxygen or sulphur.

The abovementioned general or preferred radical definitions apply both to the end products of the formula (I) and correspondingly to the starting materials or intermediates required in each case for the preparation.

Specific examples of the compounds according to the invention are the sulphonylbenzazolones listed in the tables below:

TABLE 1
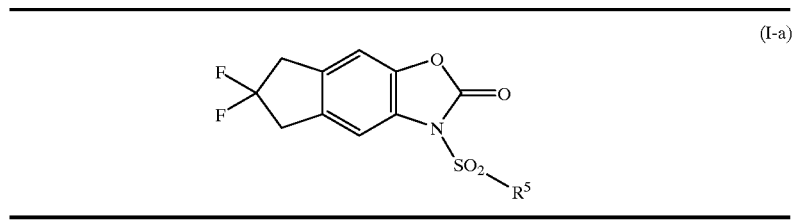
(I-a)
where R⁵ represents the following substituents:
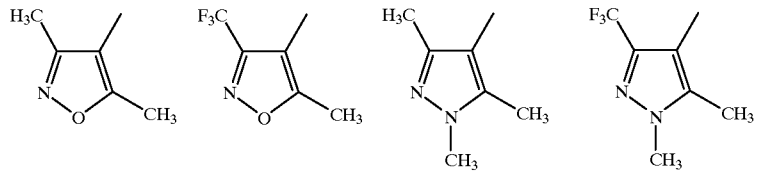
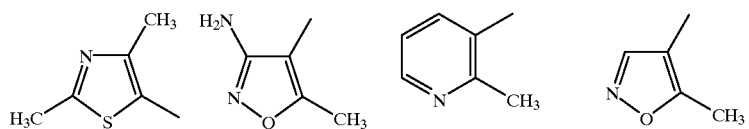
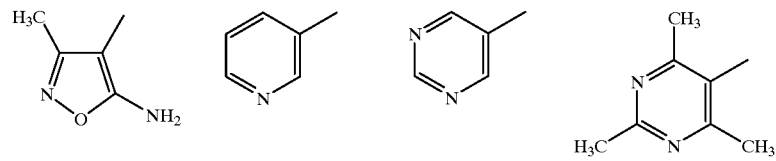
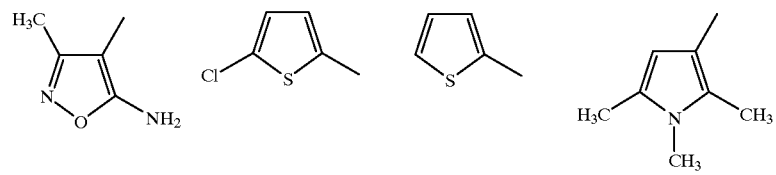
TABLE 2
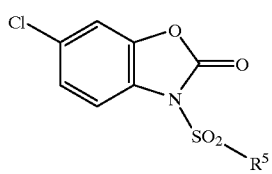
(I-b)
where R⁵ represents the substituents listed in Table 1.
TABLE 3
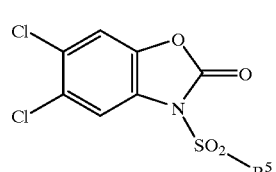
(I-c)

where R⁵ represents the substituents listed in Table 1.

TABLE 4

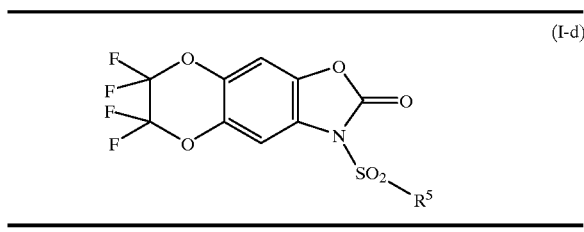

(I-d)

where R⁵ represents the substituents listed in Table 1.

TABLE 5

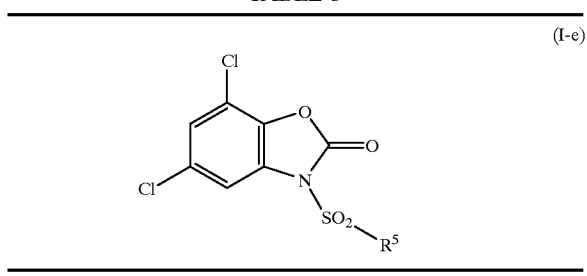

(I-e)

where R⁵ represents the substituents listed in Table 1.

TABLE 6

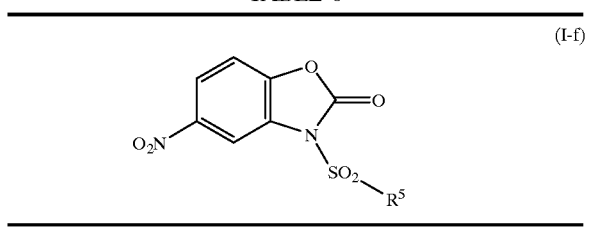

(I-f)

where R⁵ represents the substituents listed in Table 1.

TABLE 7

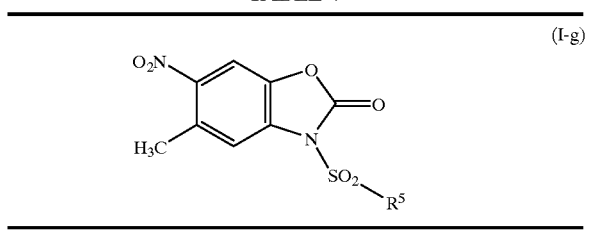

(I-g)

where R⁵ represents the substituents listed in Table 1.

TABLE 8

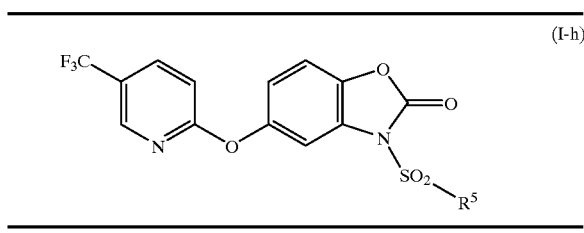

(I-h)

where R⁵ represents the substituents listed in Table 1.

TABLE 9

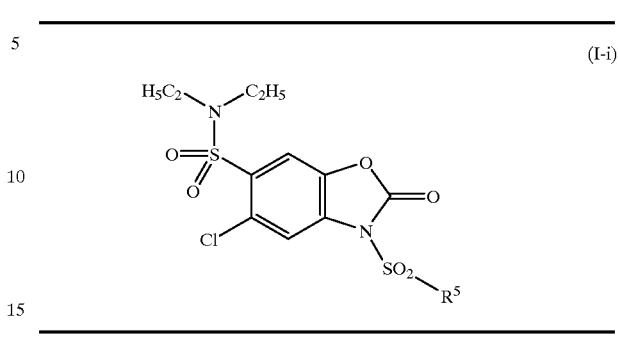

(I-i)

where R⁵ represents the substituents listed in Table 1.

TABLE 10

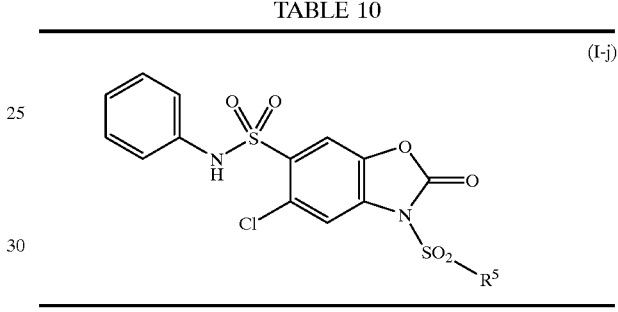

(I-j)

where R⁵ represents the substituents listed in Table 1.

TABLE 11

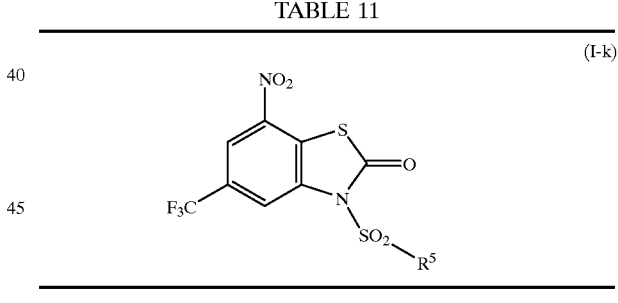

(I-k)

where R⁵ represents the substituents listed in Table 1.

TABLE 12

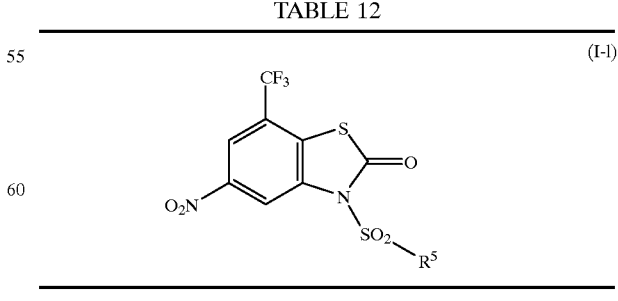

(I-l)

where R⁵ represents the substituents listed in Table 1.

TABLE 13

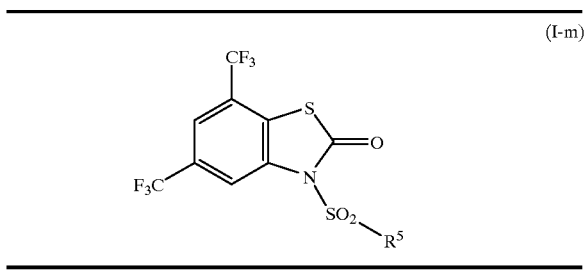

(I-m)

where R⁵ represents the substituents listed in Table 1.

Using for example 2H-benzoxazol-2-one and 3,5-dimethyl-isoxazole-4-sulphonyl chloride as starting materials, the course of the process according to the invention can be illustrated by the following scheme:

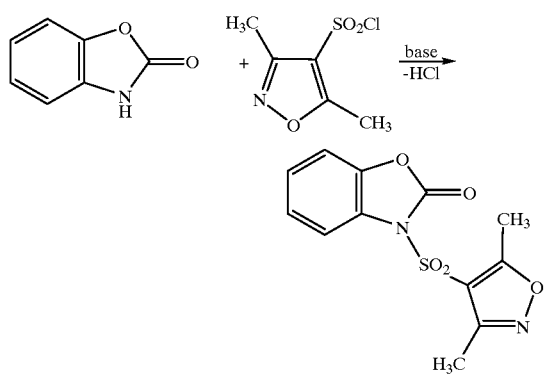

The benzazolones required as starting materials for carrying out the process according to the invention are defined in a general way by the formula (II). In this formula, $R^1$, $R^2$, $R^3$, $R^4$ and Q each preferably or in particular have those meanings already given in connection with the description of the compounds of the formula (I) according to the invention as preferred or as particularly preferred for $R^1$, $R^2$, $R^3$, $R^4$ and Q.

The benzazolones of the formula (II) are known or can be prepared by known methods (cf. Chem. Ber. 93 (1960) 1331–1339; J. Med. Chem. 9 (1966) 719; Heterocycles 24 (1986) 1625; J. Heterocycl. Chem. 28 (1991) 933; Synthesis 1984, 254 and U.S. Pat. No. 2,922,794).

The sulphonyl halides further required as reaction components for carrying out the process according to the invention are defined in a general way by the formula (III). In this formula, $R^5$ preferably or in particular has those meanings already given in connection with the description of the compounds of the formula (I) according to the invention as preferred or as particularly preferred for $R^5$. X preferably represents chlorine.

The sulphonyl halides of the formula (III) are known or can be prepared by known methods (cf. J. Heterocyclic Chem. 1981, 997–1006).

Suitable diluents for carrying out the process according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decalin; furthermore halogenated hydrocarbons, such as chlorobenzene, dichlorobenzene, dichloromethane, chloroform, carbon tetrachloride, dichloroethane or trichloroethane; and also ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; furthermore ketones, such as acetone, butanone, methyl isobutyl ketone or cyclohexanone; furthermore nitrites, such as acetonitrile, propionitrile, n- or i-butyronitrile or benzonitrile; and also esters such as methyl acetate or ethyl acetate.

Suitable acid binders for carrying out the process according to the invention are all customary inorganic or organic acid acceptors. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium hydroxide, ammonium acetate or ammonium carbonate, and tertiary amines, such as trimethylamine, triethylamine, tributylamine, N,N-dimethylaniline, N,N-dimethylbenzylamine, pyridine, N-methyl-piperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the reaction is carried out at temperatures between 0° C. and 150° C., preferably between 20° C. and 120° C.

The process according to the invention is generally carried out under atmospheric pressure. However, it is also possible to work at elevated or reduced pressure, for example at a pressure between 0.1 bar and 10 bar.

When carrying out the process according to the invention, 1 to 2 mol, preferably 1 to 1.3 mol, of sulphonyl halide of the formula (III) and optionally 1.0 to 2.0 mol, preferably 1.0 to 1.3 mol, of acid acceptor are generally used per mole of benzazolone of the formula (II). Work-up is carried out by conventional methods.

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. oryzae; Pseudomonas species, such as, for example, *Pseudomonas syringae* pv. lachrymans;

Erwinia species, such as, for example, *Erwinia amylovora*;

Pythium species, such as, for example, *Pythium ultimum*;

Phytophthora species, such as, for example, *Phytophthora infestans*;

Pseudoperonospora species, such as, for example, *Pseudoperonospora humuli* or *Pseudoperonospora cubensis*;

Plasmopara species, such as, for example, *Plasmopara viticola*;

Bremia species, such as, for example, *Bremia lactucae*,

Peronospora species, such as, for example, *Peronospora pisi* or *P. brassicae*;

Erysiphe species, such as, for example, *Erysiphe graminis*;

Sphaerotheca species, such as, for example, *Sphaerotheca fuliginea*;

Podosphaera species, such as, for example, *Podosphaera leucotricha*;

Venturia species, such as, for example, *Venturia inaequalis*;

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus*;

Puccinia species, such as, for example, *Puccinia recondita*;

Sclerotinia species, such as, for example, *Sclerotinia sclerotiorum*

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Altemaria species, such as, for example, *Altemaria brassicae*; and

Pseudocercosporella species, such as, for example, *Pseudocercosporella herpotrichoides*.

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Phytophthora species. They are also very successfully used for controlling cereal diseases, such as, for example, against Erysiphe species, or for controlling rice diseases, such as, for example, against Pyricularia species.

Furthermore, the compounds according to the invention may also be employed to increase the yield of crops.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids.

Microorganisms capable of degrading or changing the industrial materials which may be mentioned are, for example, bacteria, fungi, yeasts, algae and slime organisms. The active compounds or compositions according to the invention preferably act against fungi, in particular moulds, and against slime organisms and algae.

Microorganisms of the following genera may be mentioned as examples:

Alternaria, such as *Alternaria tenuis*,

Aspergillus, such as *Aspergillus niger*,

Chaetomium, such as *Chaetomium globosum*,

Coniophora, such as *Coniophora puetana*,

Lentinus, such as *Lentinus tigrinus*,

Penicillium, such as *Penicillium glaucum*,

Polyporus, such as *Polyporus versicolor*,

Aureobasidium, such as *Aureobasidium pullulans*,

Sclerophoma, such as *Scierophoma pityophila*,

Trichoderma, such as *Trichoderma viride*,

Escherichia, such as *Escherichia coli*,

Pseudomonas, such as *Pseudomonas aeruginosa*, and

Staphylococcus, such as *Staphylococcus aureus*.

Depending on their particular physical and/or chemical properties, the active compounds can be converted to the customary formulations, such as solutions, emulsions, suspensions, powders, foams, pastes, granules, aerosols and micro-encapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:
Fungicides:
  aldimorph, ampropylfos, ampropylfos potassium, andoprim, anilazine, azaconazole, azoxystrobin,
  benalaxyl, benodanil, benomyl, benzamacril, benzamacril-isobutyl, bialaphos, binapacryl, biphenyl, bitertanol, blasticidin-S, bromuconazole, bupirimate, buthiobate,
  calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
  debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
  edifenphos, epoxiconazole, etaconazole, ethirimol, etridiazole,
  famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazolecis, furmecyclox,
  guazatine,
  hexachlorobenzene, hexaconazole, hymexazole,
  imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
  kasugamycin, kresoxim-methyl, copper preparations, such as: copper hydroxide, copper naphthenate, copper oxychloride, copper sulphate, copper oxide, oxinecopper and Bordeaux mixture,
  mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
  nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos,
pyrifenox, pyrimethanil, pyroquilon, pyroxyfur,
quinconazole, quintozene (PCNB),
sulphur and sulphur preparations,
tebuconazole, tecloftalam, tecnazene, tetcyclasis, tetraconazole, thiabendazole, thicyofen, thifluzamide, thiophanate-methyl, thiram, tioxymid, toclofos-methyl, tolylfluanid, triadimefon, triadimenol, triazbutil, triazoxide, trichlamide,
tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1 H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
isopropyl {2-methyl-1-[[[1-(4-methylphenyl)-ethyl]-amino]-carbonyl]-propyl }-carbamate,
1-(2,4-dichlorophenyl)-2-(1H-1,2,4-triazol-1-yl) ethanone-O-(phenylmethyl)-oxime,
1-(2-methyl-1-naphthalenyl)-1H-pyrrol-2,5-dione,
1-(3 ,5-dichlorophenyl)-3-(2-propenyl)-2,5-pyrrolidindione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1, 2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluorom ethoxy-4'-trifluoro-methyl-1,3-thiazole-5-carboxanilide,
2,2-dichloro-N-[1-(4-chlorophenyl)-ethyl]-1-ethyl-3-methyl-cyclopropane-carboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2, 3-d]pyrimidine-5-carbonitrile,
2-arinobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulfonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine-hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulfonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-mono-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides:
bromopol, dichlorophen, nitrapyrin, nickel dimethyldithiocarbamate, kasugamycin, octhilinone, furan-carboxylic acid, oxytetracyclin, probenazole, streptomycin, tecloftalam, copper sulphate and other copper preparations.

Insecticides/Acaricides/Nematicides:
abamectin, acephate, acrinathrin, alanycarb, aldicarb, alphamethrin, amitraz, avermectin, AZ 60541, azadirachtin, azinphos A, azinphos M, azocyclotin, Bacillus thuringiensis, 4-bromo-2-(4-chlorophenyl)-1-(ethoxymethyl)-5 -(tri-fluoro-methyl)-1H-pyrrole-3-carbonitrile, bendiocarb, benfuracarb, bensultap, betacy-fluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-promoting substances.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, spreading, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

The compositions used for the protection of industrial materials generally comprise an amount of 1 to 95%, preferably 10 to 75%, of the active compounds.

The use concentrations of the active compounds according to the invention depend on the species and the occurrence of the microorganisms to be controlled and on the composition of the material to be protected. The optimal rate of application can be determined by test series. In general, the use concentrations are in the range from 0.001 to 5% by weight, preferably 0.05 to 1.0% by weight, based on the material to be protected.

The preparation and the use of the active compounds according to the invention is illustrated by the examples below.

PREPARATION EXAMPLES

Example 1

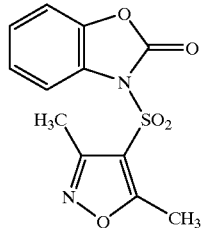

0.45 g (15 mmol) of an 80% strength suspension of sodium hydride is added to a solution of 2.0 g (15 mmol) of 3H-benzoxazol-2-one in 40 ml of absolute tetrahydrofuran. The mixture is stirred at 20° C. for 10 minutes, 3.0 g (15 mmol) of 3,5-dimethylisoxazol-4-sulphonyl chloride are added and the mixture is stirred for a further 20 hours at 20° C. The reaction mixture is then poured into 200 ml of water and extracted twice with 50 ml of diethyl ether each time. The combined organic phases are dried over sodium sulphate and concentrated under reduced pressure. The solid residue is stirred with 50 ml of petroleum ether, and the solid obtained is filtered off and dried.

3.9 g (90% of theory) of 3-(3,5-dimethyl-isoxazol-4-sulphonyl)-3H-benzoxazol-2-one are obtained as a yellow solid of melting point 133 to 135° C.

Example 2

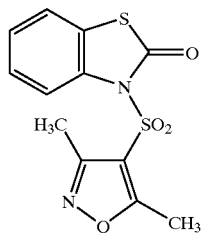

3.4 g (25 mmol) of powdered potassium carbonate and 2.9 g (15 mmol) of 3,5-dimethyl-isoxazol-4-sulphonyl chloride are added in succession to a solution of 2.3 g (15 mmol) of 3H-benzothiazol-2-one in 40 ml of absolute acetonitrile, and the mixture is stirred at 20° C. for 20 hours The reaction mixture is then poured into 200 ml of water and the solid obtained is filtered off and dried.

3.1 g (66% of theory) of 3-(3,5-dimethyl-isoxazol-4-sulphonyl)-3H-benzothiazol-2-one are obtained as a white solid of melting point 140 to 144° C.

The abovementioned methods are also used to prepare the compounds listed in the table below.

TABLE 14

(I)

| Ex. No. | $R^1$ | $R^2$ | $R^3$ | $R^4$ | Q | $R^5$ | Melting point |
|---|---|---|---|---|---|---|---|
| 3 | —H | —H | —Cl | —H | O | 3,5-dimethylisoxazol-4-yl | mp.: 164–166° C. |
| 4 | —Cl | —H | —Cl | —H | O | 3,5-dimethylisoxazol-4-yl | mp.: 183–187° C. |
| 5 | —NO$_2$ | —H | —CF$_3$ | —H | S | 3,5-dimethylisoxazol-4-yl | mp.: 129–133° C. |
| 6 | —CF$_3$ | —H | —NO$_2$ | —H | S | 3,5-dimethylisoxazol-4-yl | mp.: 210–213° C. |
| 7 | —CF$_3$ | —H | —CF$_3$ | —H | S | 3,5-dimethylisoxazol-4-yl | mp.: 152–156° C. |
| 8 | —H | —H | —H | —H | O | 5-methylisoxazol-4-yl | mp.: 121–122° C. |

TABLE 14-continued (I)

R¹, R², R³, R⁴ substituted benzoxazol-2-one (or thiazol) with N-SO₂-R⁵ substituent.

| Ex. No. | R¹ | R² | R³ | R⁴ | Q | R⁵ | Melting point |
|---|---|---|---|---|---|---|---|
| 9 | —H | —H | —Cl | —H | O | 4-methyl-5-methyl-isoxazol-3-yl | mp.: 147–148° C. |
| 10 | —H | —H | —H | —H | O | 3-amino-4-methyl-5-methyl-isoxazol-3-yl | mp.: 155–158° C. |
| 11 | —H | —H | —Cl | —H | O | 3-amino-4-methyl-5-methyl-isoxazol-3-yl | mp.: 208–209° C. |
| 12 | —NO₂ | —H | —CF₃ | —H | S | 3-amino-4-methyl-5-methyl-isoxazol-3-yl | mp.: 192–196° C. |
| 13 | —CF₃ | —H | —NO₂ | —H | S | 3-amino-4-methyl-5-methyl-isoxazol-3-yl | mp.: 187–191° C. |
| 14 | —H | —H | —H | —H | S | 3-amino-4-methyl-5-methyl-isoxazol-3-yl | mp.: 140–144° C. |
| 15 | —H | —H | —NO₂ | —H | O | 3,4-dimethyl-5-methyl-isoxazol-3-yl | mp.: 212–213° C. |

TABLE 14-continued
| Ex. No. | R¹ | R² | R³ | R⁴ | Q | R⁵ | Melting point |
|---|---|---|---|---|---|---|---|
| 16 | —H | —NO₂ | —CH₃ | —H | O | 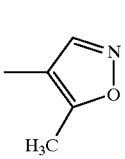 | mp.: 158–160° C. |
| 17 | —Cl | —H | —Cl | —H | O | 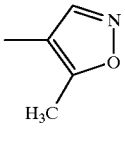 | mp.: 157–158° C. |
| 18 | —H | —H | —NO₂ | —H | O | 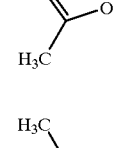 | mp.: 187–188° C. |
| 19 | —H | —NO₂ | —CH₃ | —H | O | 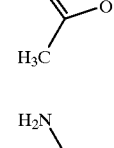 | mp.: 166–168° C. |
| 20 | —H | —Cl | —H | —H | O | 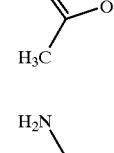 | mp.: 147–149° C. |
| 21 | —Cl | —H | —Cl | —H | O | 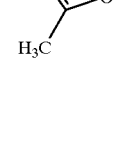 | mp.: 204–205° C. |
| 22 | —H | —H | —NO₂ | —H | O |  | mp.: 232–234° C. |

TABLE 14-continued
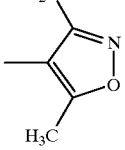
(I)
| Ex. No. | $R^1$ | $R^2$ | $R^3$ | $R^4$ | Q | $R^5$ | Melting point |
|---|---|---|---|---|---|---|---|
| 23 | —H | —NO$_2$ | —CH$_3$ | —H | O | 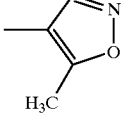 | mp.: 185–187° C. |
| 24 | —H | 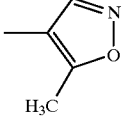 | —Cl | —H | O | 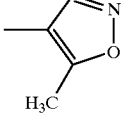 | mp.: 192–193° C. |
| 25 | —H | 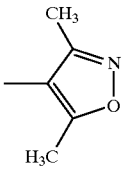 | —Cl | —H | O | 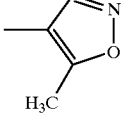 | mp.: 190–192° C. |
| 26 | —H | —Cl | —Cl | —H | O | 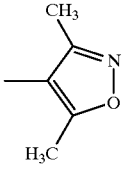 | mp.: 191–193° C. |
| 27 | —H | —H | —CH$_3$ | —H | O | 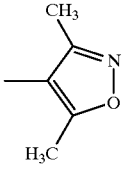 | mp.: 149° C. |

TABLE 14-continued

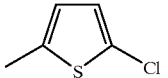

(I)

| Ex. No. | R¹ | R² | R³ | R⁴ | Q | R⁵ | Melting point |
|---|---|---|---|---|---|---|---|
| 28 | —H | —H | —CH₃ | —H | O | 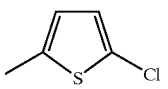 | mp.: 118–119° C. |
| 29 | —NO₂ | —H | —CF₃ | —H | S | 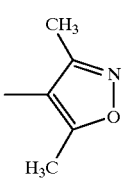 | mp.: 165° C. |
| 30 | —H | —SO₂—NH—CH₃ | —Cl | —H | O | 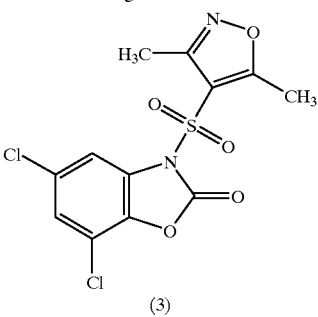 | mp.: 220° C. |

USE EXAMPLES

Example A

Phytophthora Test (tomato)/protective

Solvent: 47 parts by weight of acetone

Emulsifier: 3 parts by weight of alkylaryl polyglycol ether

To prepare a suitable active compound preparation, 1 part by weight of active compound is mixed with the stated amounts of solvent and emulsifier, and the concentrate is diluted with water to the desired concentration.

To test for protective activity, young plants are sprayed with the active compound preparation at the stated rate of application. After the spray coating has dried on, the plants are inoculated with an aqueous spore suspension of *Phytophthora infestans*.

The plants are then placed in an incubation cabinet at approximately 20° C. and a relative atmospheric humidity of 100%.

The test is evaluated 3 days after the inoculation. 0% means an efficacy which corresponds to that of the control, while an efficacy of 100% means that no disease is observed.

Active compounds, active compound application rates and test results are listed in the table below.

TABLE A

Phytophthora Test (tomato)/protective

| Active compound | Rate of application of active compound in g/ha | Efficacy in % |
|---|---|---|
| According to the invention: | | |
| (3) | 100 | 93 |
| (4) | 100 | 86 |

TABLE A-continued

Phytophthora Test (tomato)/protective

| Active compound | Rate of application of active compound in g/ha | Efficacy in % |
|---|---|---|
| (5) | 100 | 100 |
| (6) | 100 | 93 |
| (7) | 100 | 93 |

What is claimed is:

1. A sulphonylbenzazolone of the formula

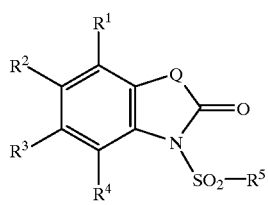

(I)

wherein $R^1$, $R^2$, $R^3$ and $R^4$ independently of each other are selected from the group consisting of hydrogen; fluorine; chlorine; bromine; iodine; cyano; nitro; straight-chain or branched alkyl having 1 to 8 carbon atoms; straight-chain or branched halogenoalkyl having 1 to 6 carbon atoms and 1 to 5 identical or different halogen atoms; straight-chain or branched alkoxy having 1 to 8 carbon atoms; straight-chain or branched halogenoalkoxy having 1 to 6 carbon atoms and 1 to 5 identical or different halogen atoms; straight-chain or branched alkylthio having 1 to 8 carbon atoms; straight-chain or branched halogenoalkylthio having 1 to 6 carbon atoms and 1 to 5 identical or different halogen atoms; straight-chain or branched alkylsulphinyl having 1 to 8 carbon atoms; straight-chain or branched halogeno-alkylsulphinyl having 1 to 6 carbon atoms and 1 to 5 identical or different halogen atoms; straight-chain or branched alkylsulphonyl having 1 to 8 carbon atoms; straight-chain or branched halogenoalkylsulphonyl having 1 to 6 carbon atoms and 1 to 5 identical or different halogen atoms; cycloalkyl having 3 to 6 carbon atoms which are unsubstituted or mono- to penta-substituted by identical or different substituents selected from the group consisting of halogen and alkyl having 1 to 4 carbon atoms; hydroxycarbonyl; alkylcarbonyl having 1 to 6 carbon atoms in a straight or branched alkyl moiety; alkoxycarbonyl having 1 to 6 carbon atoms in a straight or branched alkoxy moiety; cycloalkylcarbonyl having 3 to 6 carbon atoms in the cycloalkyl moiety; cycloalkoxycarbonyl having 3 to 6 carbon atoms in the cycloalkoxy moiety; —Z—$R^6$ or

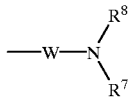

wherein $R^6$ represents aryl having 6 to 10 carbon atoms which are unsubstituted or mono- to trisubstituted by identical or different substituents selected from the group consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 6 carbon atoms and 1 to 5 identical or different halogen atoms; halogenoalkylsulphonyl having 1 to 4 carbon atoms and 1 to 5 identical or different halogen atoms;

Z represents a member selected from the group consisting of a direct bond; —$CH_2$—; O; S; $SO_2$; CO; —CO—O— wherein the oxygen atom is linked to $R^6$; —$SO_2$; —O— wherein the sulphur atom is linked to $R^6$; —S—$CH_2$—$SO_2$—O— wherein the sulphur atom of the thio group is linked to $R^6$; and —NH—$SO_2$— wherein the sulphonyl group is linked to $R^6$;

$R^7$ and $R^8$ independently of one another each represent a member selected from the group consisting of hydrogen; straight-chain or branched alkyl having 1 to 6 carbon atoms; straight-chain or branched halogenoalkyl having 1 to 6 carbon atoms and 1 to 5 identical or different halogen atoms; straight-chain or branched alkoxyalkyl having 1 to 4 carbon atoms in the alkoxy moiety and 1 to 4 carbon atoms in the alkyl moiety; alkylcarbonyl having 1 to 6 carbon atoms in a straight or branched alkyl moiety; aryl, arylcarbonyl, arylsulphonyl, arylaminocarbonyl, and arylmethylsulphonyl, wherein the aryl moiety has 6 to 10 carbon atoms and wherein the aryl moiety can be unsubstituted or mono- to trisubstituted by identical or different substituents selected from the group consisting of halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 6 carbon atoms and 1 to 5 identical or different halogen atoms; halogenoalkylsulphonyl having 1 to 4 carbon atoms and 1 to 5 identical or different halogen atoms;

W represents a direct bond, a sulphonyl group or a carbonyl group;

$R^1$ and $R^2$, or $R^2$ and $R^3$, or $R^3$ and $R^4$ together each represent an alkylene chain containing 3 or 4 carbon atoms wherein zero, one or two carbon atoms are replaced by an oxygen atom and wherein the alkylene chain is unsubstituted or mono- to hexa-substituted by a substituent selected from the group consisting of halogen, alkyl having 1 to 4 carbon atoms and halogenoalkyl having 1 to 4 carbon atoms and 1 to 5 halogen atoms;

$R^5$ represents isoxazolyl which may be substituted with from zero to three substituents selected from the group consisting of halogen; cyano; nitro; amino; hydroxyl; formyl; carboxyl; carbamoyl; thiocarbamoyl; alkyl having 1 to 4 carbon atoms; alkoxy having 1 to 4 carbon atoms; alkylthio having 1 to 4 carbon atoms; alkylsulphonyl having 1 to 4 carbon atoms; halogenoalkyl having 1 to 4 carbon atoms and 1 to 5 halogen atoms; halogenoalkoxy having 1 to 4 carbon atoms and 1 to 5 halogen atoms; halogenoalkylthio having 1 to 4 carbon atoms and 1 to 5 halogen atoms; halogenoalkylsulphonyl having 1 to 4 carbon atoms and 1 to 5 halogen atoms; alkylamino having 1 to 4 carbon atoms; dialkylamino having 1 to 4 carbon atoms in each of the two alkyl groups; alkylcarbonyl having 1 to 4 carbon atoms; alkylcarbonyloxy having 1 to 4 carbon atoms; alkoxy-carbonyl having 1 to 4 carbon atoms in the alkoxy moiety; alkylsulphonyloxy having 1 to 4 carbon atoms; hydroximinoalkyl having 1 to 4 carbon atoms; alkoximinoalkyl having 1 to 4 carbon atoms in each of the two alkyl groups; halogenoalkoxycarbonyl having 1 to 4 carbon atoms and 1 to 5 halogen atoms; and cycloalkyl having 3 to 6 carbon atoms; and Q represents oxygen.

2. A process for the preparation of the sulphonlybenzazolone of claim 1 comprising reacting a benzazolone of the formula

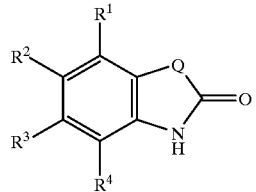

wherein
$R^1$, $R^2$, $R^3$, $R^4$ and Q are as defined in claim 12 with a sulphonyl halide of the formula
$R^5$—$SO_2$—X, wherein X represents halogen and $R^5$ is as defined in claim 1.

3. A method for controlling undesirable microorganisms in crop protection and in the protection of materials, comprising the step of applying a microbiocidally effective amount of the sulphonylbenzazolone of claim 1 to the microorganisms and/or their habitat.

4. A microbiocidal composition comprising an effective amount of the sulphonylbenzazolone of claim 1 in admixture with a diluent and/or an emulsifier.

5. A sulponylbenzazolone of the formula

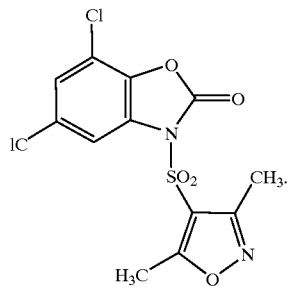

* * * * *